United States Patent
Silverman et al.

(10) Patent No.: US 11,304,419 B2
(45) Date of Patent: Apr. 19, 2022

(54) METHODS TO INDUCE HEAT STRESS TOLERANCE IN PLANTS

(71) Applicant: Valent BioSciences LLC, Libertyville, IL (US)

(72) Inventors: Franklin Paul Silverman, Highland Park, IL (US); Srirama Krishna Reddy, Libertyville, IL (US)

(73) Assignee: VALENT BIOSCIENCES LLC, Libertyville, IL (US)

( * ) Notice: Subject to any disclaimer, the term of this patent is extended or adjusted under 35 U.S.C. 154(b) by 0 days.

(21) Appl. No.: 17/180,131

(22) Filed: Feb. 19, 2021

(65) Prior Publication Data

US 2021/0259252 A1 Aug. 26, 2021

Related U.S. Application Data

(60) Provisional application No. 62/979,138, filed on Feb. 20, 2020.

(51) Int. Cl.
 *A01H 6/46* (2018.01)
 *A01N 53/00* (2006.01)

(52) U.S. Cl.
 CPC .................. *A01N 53/00* (2013.01)

(58) Field of Classification Search
 CPC .............................. A01N 53/00; A01P 21/00
 USPC .......................................................... 504/320
 See application file for complete search history.

(56) References Cited

PUBLICATIONS

Hassan et al. ACC deaminase and /or nitrogen fixing rhizobacteria and growth of wheat (*Triticum aestivum* L.) Journal of soil science and plant nutrition vol. 15 No. 1 2015.*
Larkindal et al. Thermotolerance and antioxidant system in Agrostis stoniifera. Involvement of salicylic acid calcium hydrogen peroxide, and ethylene J.Plant Physiol. 161 505-413 2004.*
1-aminocyclopropane-1-carboxylic acid 9acc0 in plants: more than just the precursor of ethylene! Frontier in Plant Science Bram Van de poel et al. 2014.*
Phloem Transport and Conjugation of Foliar Applied 1-aminocyclopropane-1-carboxylic acid in Cotton. Morris et al. J. Plant Physiol. vol. 146 pp. 429-436 (1995).*
Tack J., et al., Effect of warming temperatures on US wheat yields Proc Natl Acad Sci U S A. Jun. 2, 2015;112 (22):6931-6.
Ababaei B. and Chenu K., Heat shocks increasingly impede grain filling but have little effect on grain setting across the Australian wheatbelt, Agr. For. Meterol., Jan. 2020; 284, 107889.
Hays D.B. et al., Heat stress induced ethylene production in developing wheat grains induces kernel abortion and increased maturation in a susceptible cultivar, Plant Sci, 2007, 172, 1113-1123.
Valluru R., et al., Phenotypic and genome-wide association analysis of spike ethylene in diverse wheat genotypes under heat stress, New Phytologist, 2016, doi: 10.1111/nph. 14367, 1-13.
Miller T.D., Growth Stages of Wheat: Identification and Understanding Improve Crop Management, Texas A&M Agrilife Ext. SCS-1999-16.

* cited by examiner

*Primary Examiner* — Annette H Para
(74) *Attorney, Agent, or Firm* — Wood, Phillips, Katz, Clark & Mortimer

(57) ABSTRACT

The present invention is directed to methods of improving heat stress tolerance in plants comprising applying an effective amount of 1-amino-1-cyclopropanecarboxylic acid to the plant.

3 Claims, No Drawings

METHODS TO INDUCE HEAT STRESS TOLERANCE IN PLANTS

FIELD OF THE INVENTION

The present invention is directed to methods of improving heat stress tolerance in plants comprising applying an effective amount of 1-amino-1-cyclopropanecarboxylic acid to the plant.

BACKGROUND OF THE INVENTION

Temperatures are increasing worldwide and have been predicted to continue rising through the rest of the century. This increase in temperature will cause heat stress in crops including wheat. See, Tack J., et al., Effect of warming temperatures on US wheat yields *Proc Natl Acad Sci USA.* 2015 Jun. 2; 112(22):6931-6. Heat stress is particularly threatening to wheat production when the stress occurs during reproductive and grain-filling phases. See, Ababaei B. and Chenu K., Heat shocks increasingly impede grain filling but have little effect on grain setting across the Australian wheatbelt, *Agr. For. Meterol.,* 2020 January; 284, 107889.

Heat stress is thought to reduce the ability of the plant to photosynthesize by limiting its metabolic rate and damaging chloroplasts. This reduction in photosynthetic capacity results in reduced grain yield. Reduced grain yield is costly to both the farmers and the population as a whole. As worldwide population increases so does the need for increased crop production. Thus, improving heat stress tolerance in crops such as wheat is both beneficial and necessary to the survival of the world population.

1-amino-1-cyclopropanecarboxylic acid ("ACC") is a product of the enzyme ACC synthase and acts as a precursor for the biosynthesis of ethylene in plants. Ethylene has been shown to be involved in several plant responses including stress, fruit set, leaf abscission, anthesis, and senescence. Because of its role as an ethylene precursor ACC has been used in agriculture to induce ethylene responsive events. However, ACC has not been shown to induce heat stress tolerance in plants as diverse as wheat, corn, soybean, cotton, tomato, bean, lettuce, *Brassica napus* (e.g. canola, rapeseed, etc. . . . ) turf grasses and ornamentals. In fact, heat stress induced ethylene production in developing wheat grains induces kernel abortion and yield loss. See, Hays D. B. et al., Heat stress induced ethylene production in developing wheat grains induces kernel abortion and increased maturation in a susceptible cultivar, Plant Sci, 2007, 172, 1113-1123 and Valluru R., et al., Phenotypic and genome-wide association analysis of spike ethylene in diverse wheat genotypes under heat stress, *New Phytologist,* 2016, doi: 10.1111/nph. 14367, 1-13.

Thus, there is a need in the art for a method of improving heat stress tolerance in crops.

SUMMARY OF THE INVENTION

The present invention is directed to methods of improving heat stress tolerance in plants comprising applying an effective amount of 1-amino-1-cyclopropanecarboxylic acid ("ACC") to the plant, wherein the plant is selected from the group consisting of wheat, corn, soybean, cotton, tomato, *Brassica napus*, bean, lettuce, turf grass and an ornamental plant.

DETAILED DESCRIPTION OF THE INVENTION

Applicants have unexpectedly discovered that the application of 1-amino-1-cyclopropanecarboxylic acid ("ACC") to plants improve heat stress tolerance and results in higher grain yield.

Once planted plants undergo life stages including vegetative, reproductive, ripening and senescence. Plants commonly experience heat stress during the developmental, vegetative and reproductive stages, especially anthesis. Plants may also experience heat stress during ripening.

Wheat, specifically, undergoes several life cycle stages beginning with germination and continuing into tillering, heading, flowering and finally ripening. See Miller T. D., Growth Stages of Wheat: Identification and Understanding Improve Crop Management, *Texas A&M Agrilife Ext.* SCS-1999-16. The Feekes scale was developed to systematically describe the life cycle of the wheat plant. Feekes stage 1 describes the emergence of the wheat plant from the soil. Feekes stages 2-3 describe the tillering stage. The tillering stage is when the plant produces axillary or side shoots, which are known as tillers. The wheat plant begins to produce tillers at Feekes stage 2 and stops producing tillers at Feekes stage 3. Feekes stage 4 describes the beginning of erect growth of the wheat plant. Feekes stage 5 occurs after a chilling period and determines the number of spikelets per spike. Spikes grow from the top of each tiller and contain a number of spikelets each of which will give rise to a grain head. Tillers formed after stage 5 will not contribute to grain yield. During Feekes stages 6-9 nodes form and leaves emerge. At Feekes stage 10 the grain heads emerge, and flowering begins. Feekes stage 10 is broken down into sub-stages. Feekes stage 10.1 describes the emerging of the head. Feekes stage 10.3 describes half-complete emergence of the head. Feekes stage 10.4 describes three-fourths emergence of the head. Feekes stage 10.5 describes complete emergence of the head. At Feekes stage 10.5.1 flowering begins. This is followed by pollination and the ripening of kernels (i.e. grain) from Feekes stage 10.5.3 to Feekes stage 11.4.

Applicant has referred to soybean developmental stages throughout the application as "V" stages. The "V" stages are designated numerically as V1, V2, V3, etc. In this identification system of V(n), (n) represents the number of trifoliolate leaves that have unfolded. Each leaf stage is defined according to the uppermost leaf that has fully-expanded.

As used herein, the term "heat stress" is defined as the exposure of the plant to temperatures above 24° C. In a preferred embodiment, the term "heat stress" may include the exposure of the plant to temperatures above 25° C., above 26° C., above 27° C., above 28° C., above 29° C. or above 30° C. Heat stress may occur either during the day or at night. Heat stress during night may occur at lower temperatures than heat stress during the day for the same plant.

As used herein, the term "improving" is defined as increasing growth and or yield of the plant exposed to heat stress. Measurement of growth and or yield includes, but is not limited to, measurements taken during vegetative stages of growth including, but not limited to, fresh weight of biomass, total reproductive tiller number, percent reproductive tillers, canopy density and total dry weight of biomass and measurements taken during reproductive stages including, but not limited to, total spike number, spike weight, yield per spike, grain weight and harvest index.

As used herein, all numerical values relating to amounts, ratios, weight percentages and the like are defined as "about" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

The term "effective amount" means the amount of the formulation that will improve the heat stress tolerance. The "effective amount" will vary depending on the type of plants being treated, the severity of the heat stress, the result desired, and the life stage of the plant during treatment, among other factors. Thus, it is not always possible to specify an exact "effective amount."

The articles "a," "an" and "the" are intended to include the plural as well as the singular, unless the context clearly indicates otherwise. For example, some methods of the present invention are directed to improving heat stress in "wheat" but this can include control of multiple wheat plants (such as a more than one wheat plant or more than one wheat species).

In one embodiment, the present invention is directed to methods of improving heat stress tolerance in plants comprising applying an effective amount of ACC to the plant, wherein the plant is selected from the group consisting of wheat, corn, soybean, cotton, tomato, *Brassica napus*, bean, lettuce, turf grass and an ornamental plant.

*Brassica napus* includes all forms, subspecies and varieties thereof including, but not limited to, annual rape, Argentine canola, canola, colza, Hanover-salad, oilseed rape, rape, rapeseed, rape kale, rutabaga, Siberian kale, summer rape, swede, Swede rape, Swedish turnip and winter rape. In a preferred embodiment, the variety of *B. napus* is canola.

In a preferred embodiment the plant is selected from the group consisting of wheat, corn, soybean, cotton, tomato, *Brassica napus*, bean, lettuce and turf grass. In a more preferred embodiment, the plant is selected from the group consisting of wheat, corn, soybean, cotton, tomato, *B. napus*, bean and lettuce. In an even more preferred embodiment, the plant is wheat, lettuce, soybean, or *B. napus*.

In a preferred embodiment, the effective amount of ACC is from about 1 to about 1,000 parts per million ("ppm"), more preferably from about 1 to about 500 ppm, even more preferably from about 10 to about 300 ppm, yet more preferably from about 30 to about 300 ppm and most preferably from about 30 to about 100 ppm.

In another embodiment, ACC is applied to the plant at a rate from about 0.001 to about 1,000 grams per hectare ("g/HA"), more preferably from about 0.028 to about 281 g/HA and even more preferably from about 0.28 to about 28 g/HA.

The methods of the present invention contemplate the application of ACC to the plant during any growth stage of the plant. In a preferred embodiment, the ACC is applied to the plant during developmental, vegetative and or reproductive stages of the plant including anthesis.

In another preferred embodiment, ACC is applied to the wheat plant from Feekes stage 2 to Feekes stage 11, even more preferably from Feekes stage 2 to Feekes stage 5 or from Feekes stage 10 to Feekes stage 11 and yet even more preferably at Feekes stage 5 or from Feekes stage 10.4 to 10.5.

In another preferred embodiment, ACC is applied to the lettuce plant during the vegetative stage, more preferably during the head formation stage also known as the rosette stage.

In another preferred embodiment, ACC is applied to the soybean plant during the vegetative stage, more preferably from stage V1 to V4.

In another preferred embodiment, ACC is applied to the *Brassica napus* plant during the reproductive stage, more preferably during the flowering stage.

The ACC of the present invention can be applied by any convenient means. Those skilled in the art are familiar with the modes of application including but not limited to, spraying, brushing, soaking, in-furrow treatments, drip irrigation, drenching, sprenching, dusting, powdering, granule application, seed treatment, pressurized liquids (aerosols), fogging or side-dressing. In a preferred embodiment, the ACC is applied to the plant as a spray and even more preferably as a foliar spray.

These representative embodiments are in no way limiting and are described solely to illustrate some aspects of the invention.

Further, the following example is offered by way of illustration only and not by way of limitation.

EXAMPLES

Example 1-Heat Stress Tolerance in Wheat Following ACC Application During Flowering Method 24 pots of Apogee wheat were grown in a greenhouse under 3 consecutive growing conditions. First, the wheat was planted in ProMix® growth media and grown for about 6 weeks in a growth cabinet at 24/18° C. day/night temperature under a 16/8 hour light/dark photoperiod. Plants were at Feekes stage 10.4-10.5 (flowering stage) following the first set of growth conditions. Next, spray applications of 0, 30 or 100 ppm ACC (n=8) were made using a tank sprayer. Next, 2 days following treatment, the plants were transferred to a growth chamber at 36/30° C. day/night temperature under a 16/8-hour light/dark photoperiod for 7 days. These conditions constitute significant heat stress. Finally, the plants were then returned to growth chamber at 24/18° C. day/night temperature under a 16/8-hour light/dark photoperiod for about 5 additional weeks. Plants were then destructively harvested and measured for total spike number, spike weight, grain weight, yield per spike, Δ spike number and harvest index. Δ spike number is calculated by subtracting the number of reproductive tillers at treatment from the number of reproductive tillers at harvest. An increase in reproductive tillers is indicative of an increase in reproductive success. Harvest index is calculated by dividing pounds of grain by the total pounds of above ground biomass. Results can be seen in Table 1, below.

TABLE 1

| n = 8 | AI (ppm) | Total Spike Number | Spike Weight (grams) | Grain Weight (grams) | Yield per Spike (grams) | Δ Spike Number | Harvest Index |
|---|---|---|---|---|---|---|---|
| Control | 0 | 5.88 | 4.97 | 2.68 | 0.45 | 1.5 | 0.29 |
| ACC | 30 | 6.25 (6.3%) | 5.39 (8.5%) | 3.1 (15.7%) | 0.5 (11.1%) | 1.75 (16.7%) | 0.32 (10.3%) |
| ACC | 100 | 6.5 (10.5%) | 5.69 (14.5%) | 3.37 (25.7%) | 0.53 (17.8%) | 2.13 (42.0%) | 0.34 (17.2%) |

( ) indicates percent increase over control

Results

As seen in Table 1, above, the application of ACC prior to heat stress resulted in increased spike number, spike weight, grain weight, yield per spike, tiller number and harvest index. These increases were dose dependent. Specifically, application of 30 ppm ACC increased spike number by 6.3%, spike weight by 8.5%, grain weight by 15.7%, yield per spike by 11.1%, tiller number by 16.7% and harvest index by 10.3% over control. Application of 100 ppm ACC increased spike number by 10.5%, spike weight by 14.5%, grain weight by 25.7%, yield per spike by 17.8%, tiller number by 42.0% and harvest index by 17.2% over control. Thus, application of ACC during the flowering stage of wheat, protected the wheat from subsequent heat stress and increased yield and reproductive success over wheat that was not treated with ACC.

Example 2-Heat Stress Tolerance in Wheat Following ACC Application at Feekes Stage 5

Method

Apogee wheat was seeded into ProMix BX (Premier Horticulture) and grown in a growth cabinet under the following conditions: 24/18° C. day/night temperature under a 16/8 hour light/dark photoperiod. Plants were evaluated at Feekes stage 5 following the first set of growth conditions on Nov. 15, 2019. Next, spray applications of 0, 0 or 100 ppm ACC (n=8) were made using a track sprayer. Next, 2 days following treatment, one set of control plants ("treatment control") and the 100 ppm ACC plants were transferred to a second growth cabinet at 34/28° C. day/night temperature under a 16/8-hour light/dark photoperiod for 4 days. These conditions constitute significant heat stress. The other set of control plants ("stress control") remained in the first growth cabinet. Finally, the plants were then returned to the first growth cabinet for about 14 days where plants reached Feekes stage 10.1 (head emergence). Plants were then destructively harvested and measured for total spike number, fresh weight, total reproductive tiller number, percent reproductive tillers, Δ canopy density and total dry weight. Percent reproductive tillers is calculated by dividing the number of reproductive tillers by the total number of spikes at harvest. Δ canopy density is calculated by subtracting the canopy density at treatment from the canopy density at harvest. Results can be seen in Table 2, below.

Results

As seen in Table 2, above, the application of ACC prior to heat stress resulted in increased fresh weight, total tiller number, % tillers, Δ canopy density and total dry weight over wheat plants subject to heat stress but not treated with ACC. % reproductive tillers were returned to within 1.1% of wheat plants grown under ideal conditions (i.e. stress control). Further, Δ canopy density was increased by 42.1% in wheat plants treated with ACC over wheat plants grown under ideal conditions. Thus, application of ACC during the vegetative growth stage of wheat, protected the wheat from subsequent heat stress and increased yield and reproductive success as compared to heat-stressed wheat that was not treated with ACC.

Example 3-Heat Stress Tolerance in Wheat Following ACC Application at Feekes Stage 5

Method

Apogee wheat was seeded into ProMix BX (Premier Horticulture) and grown in a growth cabinet under the following conditions: 24/18° C. day/night temperature under a 16/8 hour light/dark photoperiod. Plants were at Feekes stage 5 following the first set of growth conditions. Next, spray applications of 0, 0, 100 or 300 ppm ACC (n=8) were made using a track sprayer on Oct. 4, 2019. Next, 2 days following treatment, one set of control plants ("treatment control") and the 100 ppm ACC plants were transferred to a second growth cabinet at 34/28° C. day/night temperature under a 16/8-hour light/dark photoperiod for 4 days. These conditions constitute significant heat stress. The other set of control plants ("stress control") remained in the first growth cabinet. Finally, the plants were then returned to the first growth cabinet for about 14 days where plants reached Feekes stage 10.1 (head emergence). Plants were then destructively harvested and measured for total spike number, fresh weight, total reproductive tiller number, percent reproductive tillers, Δ canopy density and total dry weight. Percent reproductive tillers is calculated by dividing the number of reproductive tillers by the total number of spikes at harvest. Δ canopy density is calculated by subtracting the canopy density at treatment from the canopy density at harvest. Results can be seen in Table 3, below.

TABLE 2

| n = 8 | AI (ppm) | Total Spike Number | Fresh Weight (grams) | Total Tiller Number | % Reproductive Tillers | Δ Canopy Density | Total Dry Weight (grams) |
| --- | --- | --- | --- | --- | --- | --- | --- |
| Stress Control | 0 | 3.5 | 11.3 | 3.13 | 90.60% | 1.08 | 2.55 |
| Treatment Control | 0 | 3.25 (−7.1%) | 7.7 (−31.9%) | 2 (−36.1%) | 62.50% (−31.0%) | 1.07 (−0.9%) | 1.97 (−22.7%) |
| ACC | 100 | 3.13 (−7.1%) [−3.7%] | 9.18 (−18.8%) [19.2%] | 2.75 (−12.1%) [37.5%] | 89.60% (−1.1%) [43.4%] | 1.52 (40.7%) [42.1%] | 2.12 (−16.9%) [7.6%] |

( ) indicates percent increase over stress control

[ ] indicates percent increase over treatment control

TABLE 3

| n = 8 | AI (ppm) | Total Spike Number | Fresh Weight (grams) | Total Tiller Number | % Reproductive Tillers | Δ Canopy Density | Total Dry Weight (grams) |
|---|---|---|---|---|---|---|---|
| Stress Control | 0 | 5.63 | 17.16 | 4 | 72.10% | 2.56% | 4.56 |
| Treatment Control | 0 | 6.25 | 16.97 | 3.88 | 64.30% | 2.52% | 3.88 |
| | | (11.0%) | (−1.1%) | (−3.0%) | (−10.8%) | (−1.6%) | (−14.9%) |
| ACC | 100 | 7 | 17.95 | 4.38 | 63.80% | 2.65% | 4.31 |
| | | (24.3%) | (4.6%) | (9.5%) | (−11.5%) | (3.5%) | (−5.5%) |
| | | [12.0%] | [5.8%] | [12.9%] | [−0.8%] | [5.2%] | [11.1%] |
| ACC | 300 | 6.38 | 16.74 | 3.88 | 63.10% | 2.36% | 4.33 |
| | | (13.3%) | (−2.4%) | (−3.0%) | (−12.5%) | (−7.8%) | (−5.0%) |
| | | [2.1%] | [−1.4%] | [0%] | [−1.9%] | [−6.3%] | [11.6%] |

( ) indicates percent increase over stress control
[ ] indicates percent increase over treatment control Results As seen in Table 3, above, the application of 100 ppm ACC prior to heat stress resulted in increased spike number, fresh weight, total tiller number, Δ canopy density and total dry weight over wheat plants subject to heat stress but not treated with ACC. Application of 300 ppm ACC prior to heat stress resulted in increased spike number and total dry weight. Thus, application of ACC during the vegetative growth stage of wheat, protected the wheat from subsequent heat stress and increased yield as compared to heat-stressed wheat that was not treated with ACC.

Example 4-Heat Stress Tolerance in Lettuce Following ACC Application at Rosette Stage Method Butterhead lettuce was seeded into ProMix BX (Premier Horticulture) and grown in a greenhouse. Three weeks post-sowing the lettuce was transferred to a growth cabinet under the following conditions: 24/18° C. day/night temperature under a 16/8 hour light/dark photoperiod. Plants were at head formation (rosette) stage following the first set of growth conditions. 4 days after transfer canopy density was calculated. Next, spray applications of 0, 10, 30 or 100 ppm ACC (n=5) were made using a track sprayer on Sep. 21, 2020. Next, two days following treatment, half of the plants were transferred to a second growth cabinet at 34/30° C. day/night temperature under a 16/8-hour light/dark photoperiod for nine days. These conditions constitute significant heat stress. Plants were then destructively harvested and measured for fresh weight, size, canopy density and Δ canopy density. Δ canopy density is calculated by subtracting the canopy density at treatment from the canopy density at harvest. Results can be seen in Table 4, below.

TABLE 4

| n = 5 | AI (ppm) | Fresh Weight (grams) | Canopy Density | Δ Canopy Density |
|---|---|---|---|---|
| Stress Control | 0 | 102.72 | 17.60 | 6.82 |
| Treatment Control | 0 | 84.14 | 14.71 | 3.50 |
| | | (−18.1%) | (−16.4%) | (−48.7%) |
| ACC | 10 | 93.94 | 15.58 | 5.12 |
| | | (−8.5%) | (−11.5%) | (−24.9%) |
| | | [11.6%] | [5.9%] | [46.3%] |
| ACC | 30 | 115.11 | 16.65 | 5.08 |
| | | (12.1%) | (−5.4%) | (−25.5%) |
| | | [36.8%] | [13.2%] | [45.1%] |

TABLE 4-continued

| n = 5 | AI (ppm) | Fresh Weight (grams) | Canopy Density | Δ Canopy Density |
|---|---|---|---|---|
| ACC | 100 | 97.51 | 15.80 | 4.11 |
| | | (−5.1%) | (−10.2%) | (−39.7%) |
| | | [15.9%] | [7.4%] | [17.4%] |

( ) indicates percent increase over stress control
[ ] indicates percent increase over treatment control Results As seen in Table 4, above, the application of 10, 30 or 100 ppm ACC prior to heat stress resulted in increased fresh weight, canopy density and Δ canopy density over lettuce plants subject to heat stress but not treated with ACC. Thus, application of ACC during the vegetative growth stage of lettuce, protected the lettuce from subsequent heat stress and increased yield as compared to heat-stressed lettuce that was not treated with ACC.

Example 5-Heat Stress Tolerance in Soybean Following ACC Application Method

Williams 82 soybean was seeded into ProMix BX (Premier Horticulture) and grown in a greenhouse. When soybean plants showed a fully-expanded first trifoliate (V1 growth stage) the soybeans were measured for canopy density and grouped into treatments and replicates based on relative size. Next, spray applications of 0, 10, 30 or 100 ACC (n=5) were made using a track sprayer on Oct. 9, 2020. Following spraying, plants were moved to a growth cabinet under the following conditions: 24/18 C day night temperatures under a 16/8 light dark period. Next, 3 days following treatment, half of the plants were transferred to a second growth cabinet at 34/30° C. day/night temperature under a 16/8-hour light/dark photoperiod for six days. These conditions constitute early season heat stress. Plants were then destructively harvested and measured for fresh weight, canopy density, Δ canopy density, total dry weight and height. Results can be seen in Table 5, below.

TABLE 5

| n = 5 | AI (ppm) | Fresh Weight (grams) | Canopy Density | Δ Canopy Density | Total Dry Weight (grams) | Height (cm) |
|---|---|---|---|---|---|---|
| Stress Control | 0 | 14.95 | 7.2 | 2.18 | 2.65 | 31.58 |

TABLE 5-continued

| n = 5 | AI (ppm) | Fresh Weight (grams) | Canopy Density | Δ Canopy Density | Total Dry Weight (grams) | Height (cm) |
|---|---|---|---|---|---|---|
| Treatment Control | 0 | 18.64 (24.7%) | 11.66 (61.9%) | 6.35 (191.3%) | 2.95 (11.3%) | 38.05 (20.5%) |
| ACC | 10 | 19.85 (32.8%) [6.5%] | 13.24 (83.9%) [13.6%] | 7.77 (256.4%) [22.4%] | 3.15 (18.9%) [6.8%] | 41.07 (30.1%) [7.9%] |
| ACC | 30 | 20.33 (36.0%) [9.1%] | 12.68 (76.1%) [8.7%] | 7.19 (229.8%) [13.2%] | 3.25 (22.6%) [10.2%] | 38.25 (21.1%) [0.5%] |
| ACC | 100 | 19.25 (28.8%) [3.3%] | 10.90 (51.4%) [−6.5%] | 5.36 (145.9%) [−15.6%] | 3.08 (16.2%) [4.4%] | 37.95 (20.2%) [−0.3%] |

( ) indicates percent increase over stress control
[ ] indicates percent increase over treatment control Results As seen in Table 5, above, the application of 10 and 30 ppm ACC prior to heat stress resulted in increased fresh weight, canopy density, Δ canopy density, total dry weight and height over soybean plants subject to heat stress but not treated with ACC. Application of 100 ppm ACC prior to heat stress resulted in increased total dry weight. Thus, application of ACC during the vegetative growth stage of soybean, protected the soybean from subsequent heat stress and increased yield as compared to heat-stressed soybean that was not treated with ACC.

Example 6-Heat Stress Tolerance in *Brassica napus* Following ACC Application Method A dwarf variety of *Brassica napus* commonly used as an experimental model for the canola variety of *B. napus* was seeded into ProMix BX (Premier Horticulture) and grown in a greenhouse. Next, spray applications of 0, 10, 100 or 300 ppm ACC (n=10) were made using a track sprayer when six days after *B. napus* plants initiated flowering. Following spraying, plants were moved to a growth cabinet under the following conditions: 24/18 C day night temperatures under a 16/8 light dark period. Next, 2 days following treatment, half of the plants were transferred to a second growth cabinet at 36/30° C. day/night temperature under a 16/8-hour light/dark photoperiod for seven days. These conditions constitute early season heat stress. At all times flowers and pods were pruned to keep the number of pods to about 10. Plants were then destructively harvested and measured for seed yield, seed numbers, seed yield per pod, seed number per pod and single seed weight. Results can be seen in Table 6, below.

TABLE 6

| n = 10 | AI (ppm) | Seed Yield per Pod (grams) | Seed Number per Pod | Single Seed Weight (grams) |
|---|---|---|---|---|
| Treatment Control | 0 | 0.029 | 13.9 | 0.0021 |
| ACC | 10 | 0.029 [0%] | 14.8 [6.5%] | 0.0019 [−9.5%] |
| ACC | 30 | 0.033 [13.8%] | 15.1 [8.6%] | 0.0021 [0%] |
| ACC | 100 | 0.036 [24.1%] | 17.4 [25.2%] | 0.0020 [−4.8%] |
| ACC | 300 | 0.030 [3.4%] | 15.6 [12.2%] | 0.0019 [−9.5%] |

[ ] indicates percent increase over treatment control

Results

As seen in Table 6, above, the application of 30, 100 or 300 ppm ACC prior to heat stress resulted in increased seed yield per pod and seed number per pod over *B. napus* plants subject to heat stress but not treated with ACC. Application of 10 ppm ACC prior to heat stress resulted in increased seed number per pod. Thus, application of ACC during the early reproductive growth stage of *B. napus* dwarf variety, protected the plant from subsequent heat stress and increased yield as compared to heat-stressed *B. napus* dwarf variety that was not treated with ACC.

What is claimed is:

1. A method of improving heat stress tolerance in wheat plants comprising applying an effective amount of 1-amino-1-cyclopropanecarboxylic acid (ACC) to the wheat plant, wherein the ACC is applied to the wheat plant from Feekes stage 2 to Feekes stage 11.

2. The method of claim 1, wherein the ACC is applied to the wheat plant at Feekes stage 5.

3. The method of claim 1, wherein the ACC is applied to the wheat plant from Feekes stage 10.4 to Feekes stage 10.5.

* * * * *